(12) United States Patent
Phan et al.

(10) Patent No.: US 8,372,117 B2
(45) Date of Patent: Feb. 12, 2013

(54) MULTI-LEVEL INTERSPINOUS IMPLANTS AND METHODS OF USE

(75) Inventors: Christopher U. Phan, San Leandro, CA (US); David M. Schummers, San Francisco, CA (US)

(73) Assignee: Kyphon Sarl, Neuchatel (CH)

( * ) Notice: Subject to any disclaimer, the term of this patent is extended or adjusted under 35 U.S.C. 154(b) by 613 days.

(21) Appl. No.: 12/479,072

(22) Filed: Jun. 5, 2009

(65) Prior Publication Data
US 2010/0312277 A1   Dec. 9, 2010

(51) Int. Cl.
*A61B 17/70* (2006.01)
(52) U.S. Cl. ............................................ 606/248
(58) Field of Classification Search ........... 606/246–279
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

Anasetti et al., "Spine Stability After Implantation of an Interspinous Device: An In Vitro and Finite Element Biomechanical Study," J. Neurosurg. Spine, Nov. 2010, vol. 13, pp. 568-575.

(Continued)

*Primary Examiner* — Eduardo C Robert
*Assistant Examiner* — Tara Carter (57) ABSTRACT

Multi-level interspinous implants and methods of using the implants with the implants generally include a first member for placement in a first interspinous space and a second member for placement in a second interspinous space. An elongated connector extends from one of the members and is sized to fit in a slot in the other member. Each of the first and second members may include a distal wing, a body, and a proximal wing. The members may also be positioned in a closed orientation for insertion into the patient and a deployed orientation with the distal and proximal wings extending outward along lateral sides of respective spinous processes. The connector may extend outward from the proximal wing of one of the members and away from the other member when that member is in the closed orientation. The connector may be rotated and inserted into the slot where it is secured when that member from which is extends is moved to the deployed orientation.

19 Claims, 7 Drawing Sheets

U.S. PATENT DOCUMENTS

| | | |
|---|---|---|
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,436,140 B1 | 8/2002 | Liu et al. |
| 6,440,169 B1 | 8/2002 | Elberg et al. |
| 6,447,513 B1 | 9/2002 | Griggs |
| 6,447,546 B1 | 9/2002 | Bramlet et al. |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |

| Patent No. | Date | Inventor |
|---|---|---|
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0143266 A1 | 7/2004 | Kozak et al. |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0271194 A1 | 11/2006 | Zucherman et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0161993 A1 | 7/2007 | Lowery et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0179500 A1 | 8/2007 | Chin et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233082 A1 | 10/2007 | Chin et al. |
| 2007/0233084 A1 | 10/2007 | Betz et al. |
| 2007/0233088 A1 | 10/2007 | Edmond |
| 2007/0233089 A1 | 10/2007 | DiPoto et al. |

| | | |
|---|---|---|
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270840 A1 | 11/2007 | Chin et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0140125 A1 | 6/2008 | Mitchell et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0177306 A1 | 7/2008 | Lamborne et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0228225 A1 | 9/2008 | Trautwein et al. |
| 2008/0234824 A1 | 9/2008 | Youssef et al. |
| 2008/0243186 A1* | 10/2008 | Abdou ................ 606/246 |
| 2008/0255668 A1 | 10/2008 | Fallin et al. |
| 2008/0255669 A1 | 10/2008 | Fallin et al. |
| 2008/0262617 A1 | 10/2008 | Froehlich et al. |
| 2008/0281359 A1* | 11/2008 | Abdou ................ 606/246 |
| 2008/0281360 A1 | 11/2008 | Vittur et al. |
| 2008/0281361 A1 | 11/2008 | Vittur et al. |
| 2008/0281423 A1 | 11/2008 | Sheffer et al. |
| 2009/0062915 A1 | 3/2009 | Kohm et al. |
| 2009/0099170 A1 | 4/2009 | Johnson et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2009/0292316 A1 | 11/2009 | Hess |
| 2009/0326538 A1 | 12/2009 | Sennett et al. |
| 2010/0121379 A1 | 5/2010 | Edmond |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |

FOREIGN PATENT DOCUMENTS

| | | |
|---|---|---|
| DE | 4012622 C1 | 7/1991 |
| DE | 202006018978 U1 | 2/2007 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007/052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Bellini et al., "Biomechanics of the Lumbar Spine After Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. 5298-5301, vol. 16, No. 6, Supplement.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," Spine, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring—Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," Spine, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 o Congresso, Jun. 21-23, 2001, Paestum.
Petrini et al., "Stabilizzazione Elastica," Patologia Degenerative del Rachide Lombare, Oct. 5-6, 2001, Rimini.
Porter, "Spinal Stenosis and Neurogenic Claudication," Spine, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," Spine, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," Spine, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrodèse," La Revue de Medécine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.
Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.
Taylor, "Présentation à un an d'un dispositif amortissant d'assistance discale," 5èmes journées Avances & Controverses en pathologie rachidienne, Oct. 1-2, 1998, Faculté Libre de Médecine de Lille.
Tsuji et al., "Ceramic Interspinous Block (CISB) Assisted Anterior Interbody Fusion," J. Spinal Disorders, 1990, pp. 77-86, vol. 3, No. 1.
Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.
Voydeville et al., "Experimental Lumbar Instability and Artificial Ligament," Eur. J. Orthop. Surg. Traumatol., Jul. 15, 2000, pp. 167-176, vol. 10.
Voydeville et al., "Lumbar Instability Treated by Intervertebral Ligamentoplasty with Smooth Wedges," Orthopédie Traumatologie, 1992, pp. 259-264, vol. 2, No. 4.
Waldemar Link, "Spinal Surgery: Instrumentation and Implants for Spinal Surgery," 1981, Link America Inc., New Jersey.
Wiltse et al., "The Treatment of Spinal Stenosis," Clinical Orthopaedics and Related Research, Urist, ed., Mar.-Apr. 1976, pp. 83-91, No. 115.
Wisneski et al., "Decompressive Surgery for Lumbar Spinal Stenosis," Seminars in Spine Surgery, Wiesel, ed., Jun. 1994, pp. 116-123, vol. 6, No. 2.
Zucherman et al., "Clinical Efficacy of Spinal Instrumentation in Lumbar Degenerative Disc Disease," Spine, Jul. 1992, pp. 834-837, vol. 17, No. 7.

* cited by examiner

MULTI-LEVEL INTERSPINOUS IMPLANTS AND METHODS OF USE

BACKGROUND

A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Procedures to remedy back problems sometimes include insertion of implants over multiple spinal levels. The procedures may insert multiple implants each configured for placement at one of the spinal levels. The anatomy of the vertebral members that form the spine dictate the dimensions and physical characteristics of each of the implants. In some instances, a first spinal level may include vertebral members that provide a secure anchor for a first implant. However, the vertebral members at a second spinal level may not provide a secure anchor for a second implant. Therefore, this second implant may not be properly positioned at the second spinal level, or the second implant may be prone to move after it is implanted in the patient.

One application of a multi-level procedure is the treatment of spinal stenosis at the L4/L5 and L5/S1 levels. Treatment of spinal stenosis at these spinal levels may include placement of multiple interspinous implants. The anatomy of most patients provides for a secure anchor of an interspinous implant at the L4/L5 level. However, there is a large variation in the S1 spinous process in the general population. Many patients do not have a prominent S1 spinous process that provides a secure anchor for an interspinous implant at the L5/S1 level. Therefore, it would be advantageous for a multi-level procedure to utilize a secure implant at one spinal level to secure a second implant at a second spinal level to secure the second implant in the proper location and prevent unwanted movement of the second implant.

SUMMARY

The present application is directed to multi-level interspinous implants and methods of using the implants. The implants generally include a first member for placement in a first interspinous space, a second member for placement in a second interspinous space. A connector extends from one of the members and is sized to fit in a slot in the other member. Each of the first and second members may include a distal wing, a body, and a proximal wing. The members may also be positioned in a closed orientation for insertion into the patient with the distal wings aligned with the bodies to provide a reduced profile that facilitates passage of the distal wings through the interspinous space and placement of the bodies within the interspinous space. The members may also be positioned in a deployed orientation with the distal and proximal wings of each member extending outward along laterals sides of respective spinous processes. The connector may extend outward from a proximal wing of one of the members and away from the other member when that member is in the closed orientation. The connector may be rotated and inserted into the slot where it is secured when that member from which is extends is moved to the deployed orientation.

The various aspects of the various embodiments may be used alone or in any combination, as is desired.

DETAILED DESCRIPTION

Figure 1:
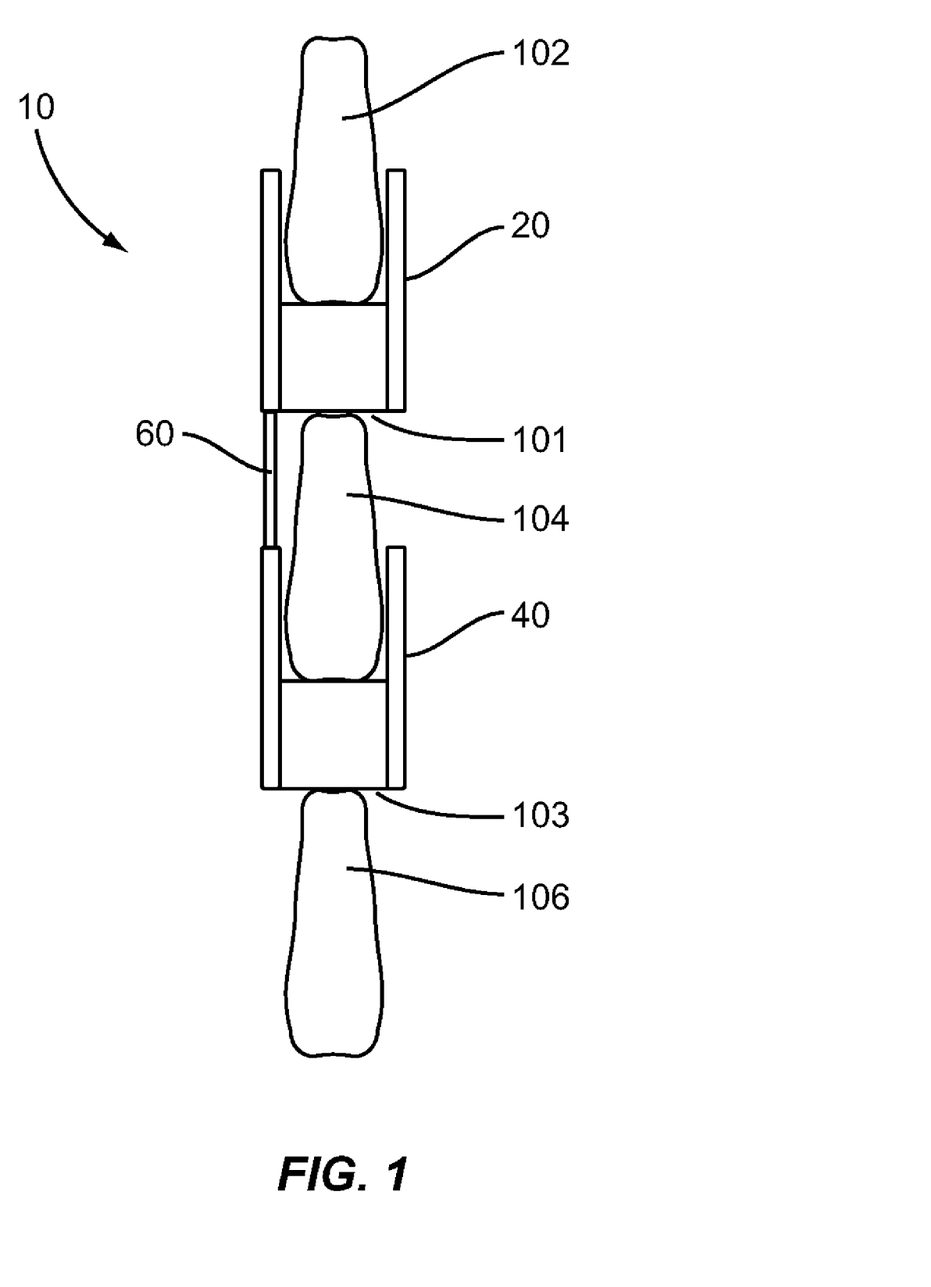
FIG. 1 is a schematic view of an interspinous support implant according to one embodiment.

The present application is directed to multi-level interspinous implants and methods for treating vertebral members over multiple spinal levels. FIG. 1 illustrates a schematic diagram of an interspinous support implant 10 that treats vertebral members at multiple spinal levels. The implant 10 includes a first member 20, a second member 40, and a connector 60. The first member 20 is positioned in a superior interspinous space 101 formed between spinous processes 102, 104. The second member 40 is positioned in an inferior interspinous space 103 formed between spinous process 104, 106. The connector extends outward from one of the members 20, 40 and is secured to the other member 20, 40. The members 20, 40 may be configured in a closed orientation with a reduced profile to facilitate insertion into the patient. After insertion and positioning in the interspinous spaces 101, 103, the members 20, 40 may be moved to an enlarged deployed orientation. The implant 10 may further configured for unilateral insertion into the patient without requiring distraction of tissue on the contralateral side.

Figure 2:
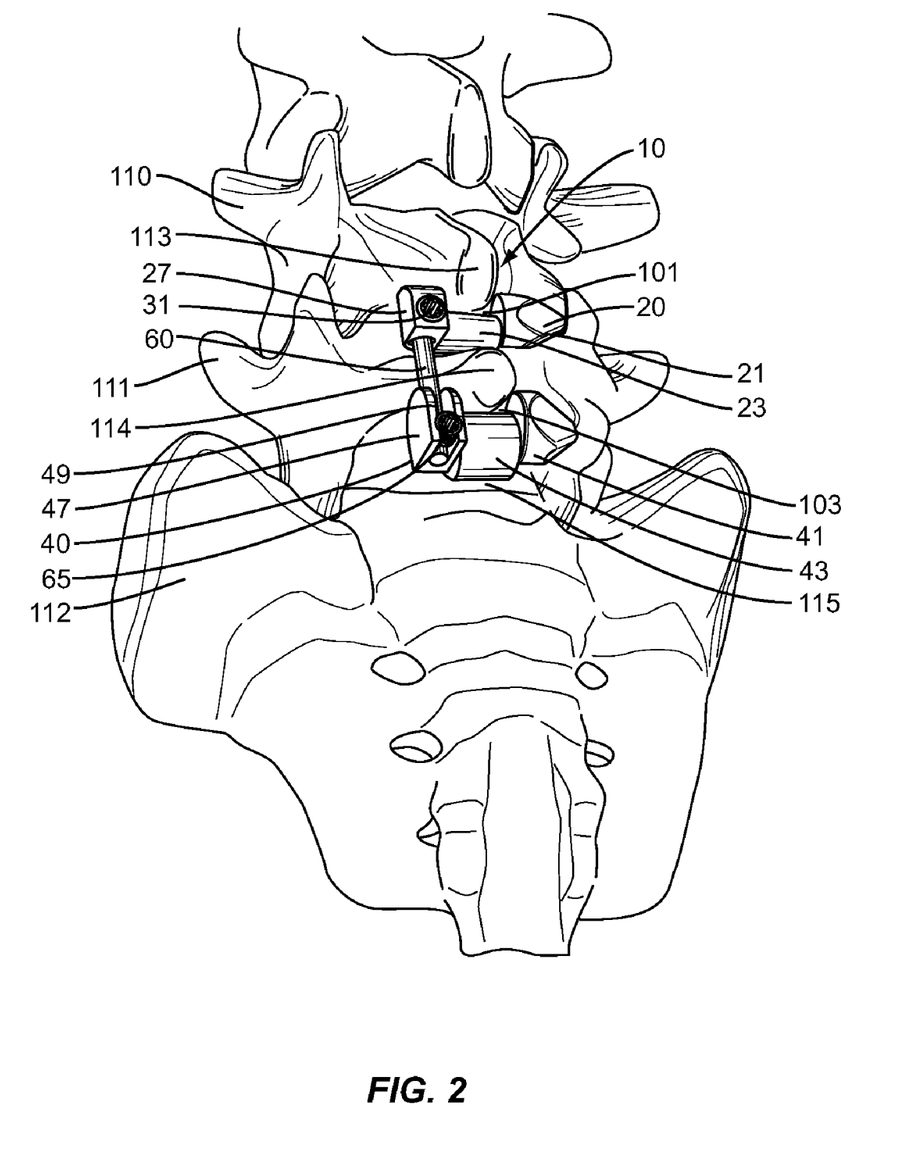
FIG. 2 perspective view of a multi-level interspinous implant positioned within a patient according to one embodiment.

FIG. 2 illustrates the implant 10 implanted in a patient with the first member 20 extending in the L4/L5 interspinous space 101 and the second member 40 extending in the L5/S1 interspinous space 103. The first member 20 anchors the second member 40 through the connector 60 to position and/or prevent movement of the second member 40. The connector 60 particularly prevents inferior migration of the second member 40 which may be prevalent in other devices because of the size of the S1 spinous process 115.

The first member 20 generally includes a distal wing 21, body 23, and a proximal wing 27 as illustrated in FIGS. 3-6. The distal wing 21 may include a tapered section that forms a pointed leading end 22. The shape facilitates insertion into and through the interspinous space 101.

Figure 3:
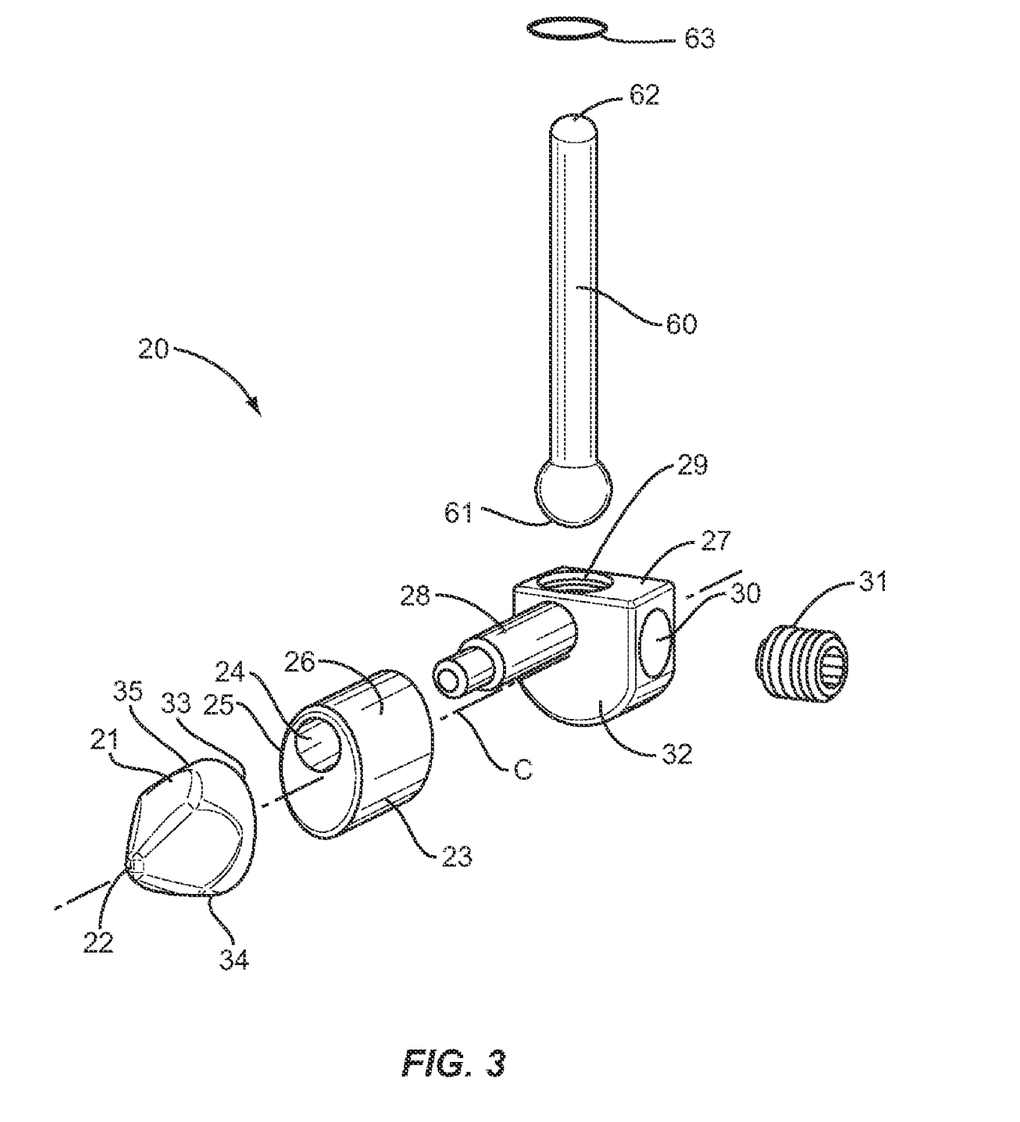
FIG. 3 is an exploded perspective view of a first member according to one embodiment.

The body 23 is sized to fit within the interspinous space 101 with the opposing sides 25, 26 contacting against the spinous processes 113, 114. In the illustrated embodiment, the body 23 includes an oval cross-sectional shape. An aperture 24 extends through the body 23 and may be positioned away from a longitudinal axis C of the body 23. The body 23 may be formed of a compressible material, or wrapped in a compressible material to provide a move secure contact against the spinous processes 113, 114.

The proximal wing 27 is positioned on an opposite side of the body 23 from the distal wing 21. The proximal wing 27 includes an extension 28 that extends outward from an inner face 32. The extension 28 includes a length to extend through the aperture 24 in the body 23 and connect to the distal wing 21. The extension 28 may include a width sized relative to the aperture 24 for the extension 28 to rotate within the aperture 24 without causing rotation of the body 23. In one embodiment, the end of the extension 28 is threaded to engage with threads in a cavity that extends into an inner face 33 of the distal wing 21. The end of the extension 28 may also be connected to the distal wing 21 by other means, including but not limited to press fit, welding, adhesive, and mechanical fasteners. The extension 28 may connect to the distal wing 21 at a point away from a mid point of the distal wing 21.

The proximal wing 27 also includes a first cavity 29 and a second cavity 30. The first cavity 29 extends into the proximal wing 27 from a first direction, and the second cavity 30 extends in from a second direction. The cavities 29, 30 are in communication within an interior of the proximal wing 27. The second cavity 30 may be threaded to receive a setscrew 31 for securing the connector 60 as will be explained below.

Figure 4:
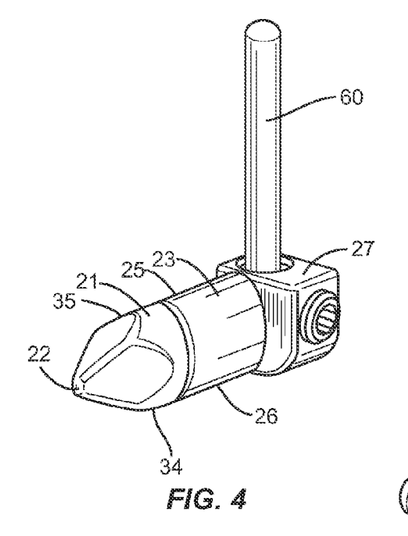
FIG. 4 is a perspective view of a first member in a closed orientation according to one embodiment.
Figure 5:
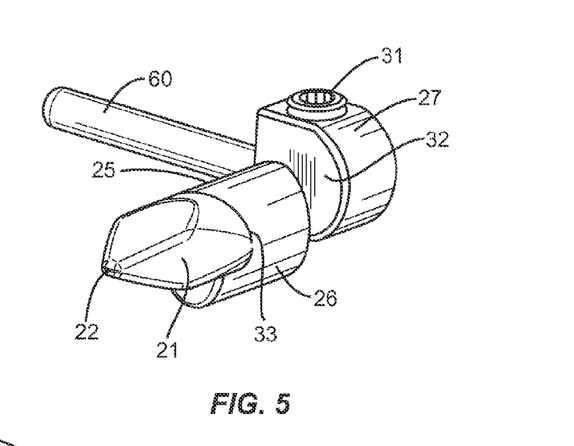
FIG. 5 is a perspective view of a first member in a deployed orientation according to one embodiment.
Figure 6:
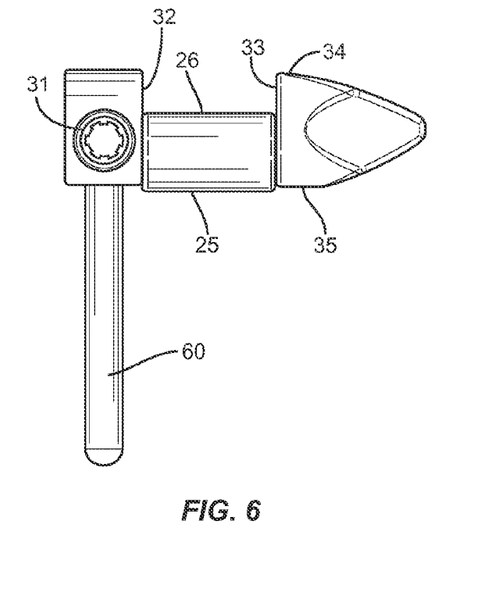
FIG. 6 is a top view of a first member in a deployed orientation according to one embodiment.

The first member 20 is adjustable from a closed orientation as illustrated in FIG. 4 to a deployed orientation as illustrated in FIGS. 5 and 6. In the closed orientation, the distal wing 21 and body 23 are aligned to form a reduced profile that facilitates insertion into the patient. The distal wing 21 may include a maximum cross-sectional profile that is larger than or equal to the body 23. In the illustrated embodiment, both include an oval cross-sectional shape and form an overall bullet shape with the tapered end of the distal wing 21 forming an insertion path that is utilized by the body 23 during insertion into the interspinous space 101. In this embodiment, the body 23 and inner end of the distal wing 21 each include a shape with a major axis and a minor axis. In the closed orientation, the distal wing 21 and body 23 are oriented with these axes being substantially aligned in the same direction.

The deployed orientation as illustrated in FIGS. 5 and 6 includes both the distal and proximal wings 21, 27 rotated to different alignments relative to the body 23. The distal wing 21 is rotated with the major axis at a non-parallel alignment relative to the major axis of the body 23. A first side 34 of the distal wing extends outward beyond the side 26 of the body 23. The section of the inner face 33 that extends outward beyond the side 26 is positioned along the lateral side of the spinous process 113. Further, the proximal wing 27 extends outward beyond the side 26 of the body 23 to be positioned along an opposite lateral side of the spinous process 113. The face 33 of the distal wing 21 and the face 32 of the proximal wing 27 are each positioned towards the spinous process 113. The body 23 is positioned in the interspinous space 101 and the side 26 contacts against an inferior side of the spinous process 113, and the opposing side 25 of the body 26 contacts against a superior side of the inferior spinous process 114. As best illustrated in FIG. 6, the side 25 may be positioned beyond the inferior sides of the distal and proximal wings 21, 27 such that the contact with the inferior spinous process 114 is limited to the body 23.

The second member 40 includes many of the same elements as the first member 20. As illustrated in FIGS. 7-10, the second member 40 generally includes a distal wing 41, body 43, and a proximal wing 47. The distal wing 41 may include a tapered section that forms a pointed leading end 42. The distal wing 41 further includes an elongated cross-sectional shape with opposing sides 54, 55 located along a major axis.

Figure 7:
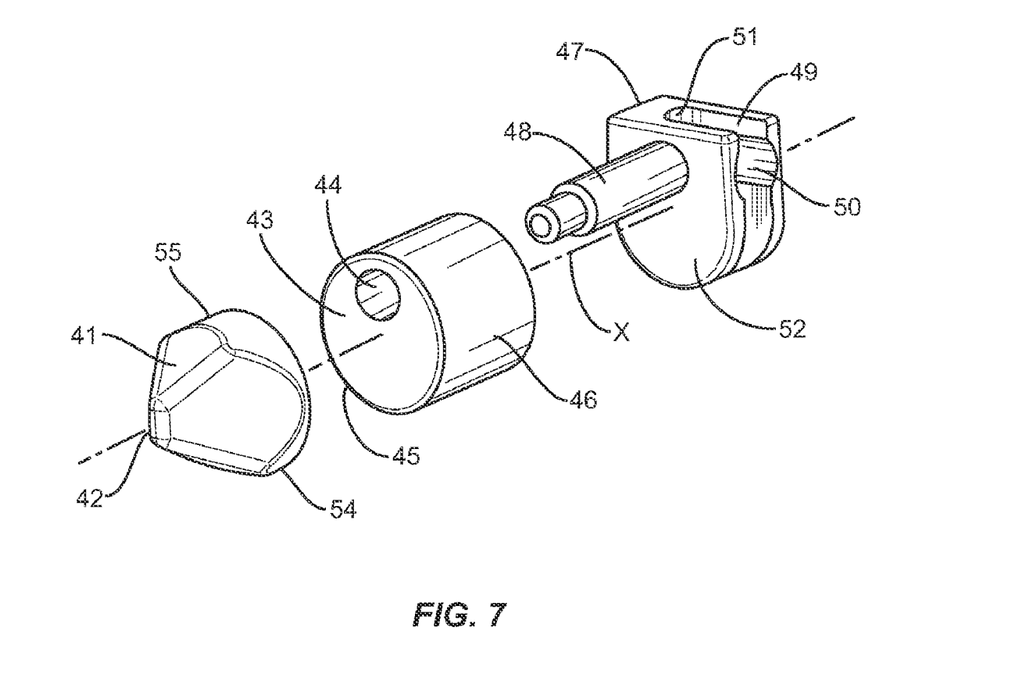
FIG. 7 is an exploded perspective view of a second member according to one embodiment.

The body 43 is sized to fit within the interspinous space 103. An aperture 44 extends through the body 43 and may be positioned away from a longitudinal axis X. The body 23 may be formed of a compressible material, or wrapped in a compressible material to provide a move secure contact against the spinous processes 114, 115.

The proximal wing 47 is positioned on an opposite side of the body 43 from the distal wing 42. The proximal wing 47 includes an extension 48 that extends outward from an inner face 52. The extension 48 includes a length to extend through the aperture 44 and connect to the distal wing 41. The end of the extension 48 may be threaded to engage with threads in an aperture that extends into an inner face 53 of the distal wing 41. The end of the extension 48 may also be connected to the distal wing 41 by other means, including but not limited to press fit, welding, adhesive, and mechanical fasteners. The extension 48 may be connected at a point on the inner face 53 at a point away from a mid point of the distal wing 41. The width of the extension 48 relative to the aperture 44 allows for the extension 48 to rotate without causing rotation of the body 43.

The proximal wing 47 also includes a slot 49 sized to receive the connector 60. The slot 49 extends into the posterior side of the proximal wing 47 and at least one of the superior and inferior sides. The slot 49 includes a bottom wall 51 positioned within the interior of the proximal wing 47. Slot 49 may also include a threaded enlarged portion 50 that is wider than the adjacent areas to receive a setscrew as will be explained below.

Figure 8:
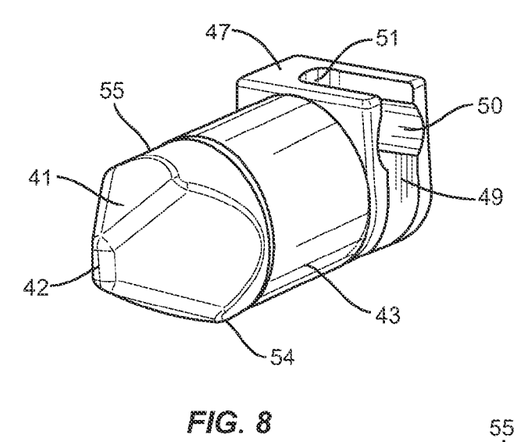
FIG. 8 is a perspective view of a second member in a closed orientation according to one embodiment.
Figure 9:
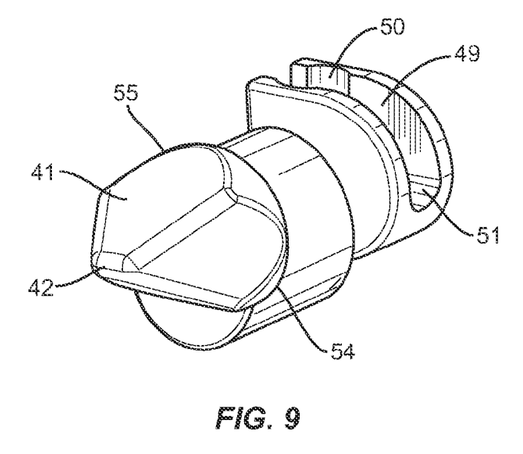
FIG. 9 is a perspective view of a second member in a deployed orientation according to one embodiment.
Figure 10:
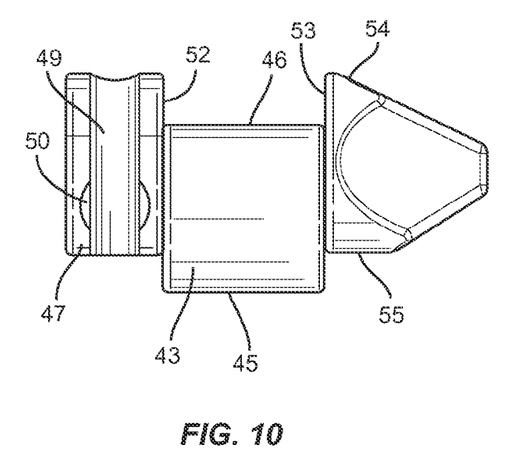
FIG. 10 is a top view of a second member in a deployed orientation according to one embodiment.

As with the first member 20, the second member 40 is adjustable from a closed orientation as illustrated in FIG. 8 to a deployed orientation as illustrated in FIGS. 9 and 10. In the closed orientation, the distal wing 41 and body 43 are aligned to form a reduced profile that facilitates insertion into the patient as explained above for the first member 20. The body 43 and inner end of the distal wing 41 may each include a shape with a major axis and a minor axis with the major axes extending in the same directions in the closed orientation.

The deployed orientation as illustrated in FIGS. 9 and 10 includes both the distal and proximal wings 41, 47 rotated to different alignments relative to the body 43. As explained above for the first member 20, the distal wing 41 is rotated with the major axis at a non-parallel alignment relative to the major axis of the body 43. A first side 54 of the distal wing extends outward beyond the side 46 of the body 43. The section of the distal wing 41 that extends outward beyond the side 46 is positioned along a first lateral side of the spinous process 114, and the section of the proximal wing 47 that extends outward beyond the side 46 is positioned along a second lateral side of the spinous process 114 to prevent lateral movement of the second member 40. The body 43 is positioned with side 46 contacting against an inferior side of the spinous process 113, and the opposing side 45 contacting against a superior side of the spinous process 115. As best illustrated in FIG. 10, the side 45 may be positioned beyond the inferior sides of the distal and proximal wings 41, 47 in the inferior direction such that the contact with the inferior spinous process 115 is limited to the body 43.

The connector 60 functions to connect the first and second members 20, 40. As best illustrated in FIG. 3, the connector 60 is substantially straight and includes a first end 61 with a rounded head and a second end 62. The rounded first end 61 is positioned within the proximal wing 27 and causes the connector 60 to be movable within a conical sweep outward from the proximal wing 27. The connector 60 may include other shapes and configurations, including a curved shape, and the first end 61 without a rounded head. A retaining clip 63 may attach to the proximal wing 27 to retain the rounded first end 61 with the proximal wing 27. The retaining clip 63 includes an aperture with a width larger than the second end 62 and smaller than the rounded head. The retaining clip 63 is attached to the proximal wing 27 to retain the rounded end 61 to the proximal wing 27. The retaining clip 63 may also prevent the connector 60 from moving outward away from the proximal wing 27. The connector 60 may be connected to the proximal wing 27 before or after insertion into the patient.

Figure 11:
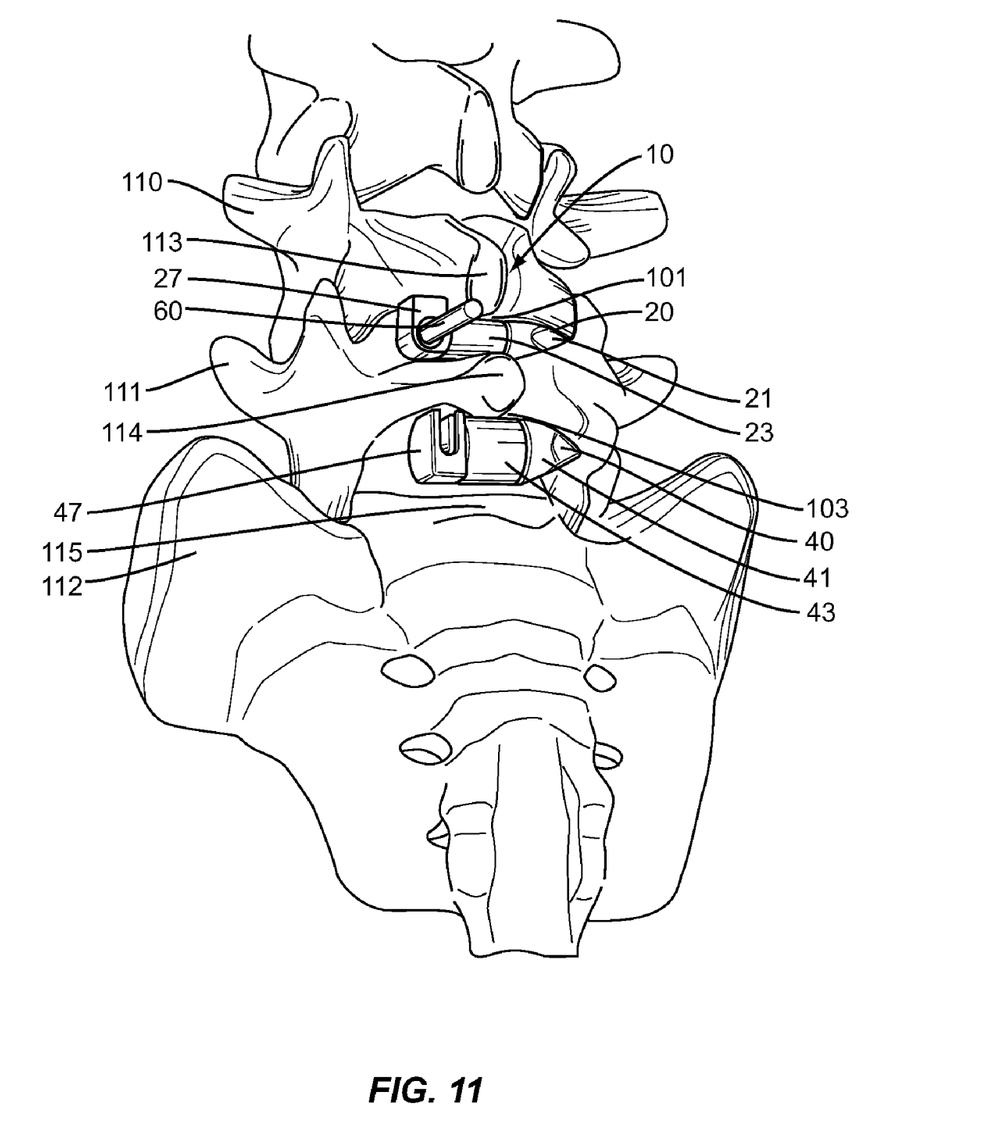
FIG. 11 is a perspective view of an implant being positioned within a patient with first and second members positioned in interspinous spaces according to one embodiment.

FIGS. 2 and 11 include a process of implanting the implant 10 into a patient. In this process, the first member 20 and second member 40 are separate when inserted into the patient. Each of the members 20, 40 are placed in their closed orientations to facilitate unilateral insertion. The distal wing 21 includes a tapered shape to ease the insertion, and the body 23 is positioned within the profile of the distal wing 21. The height of the distal wing 21 in the closed orientation allows the distal wing 21 to pass through the interspinous space 101 and be positioned on the far lateral side of the interspinous space 101. The distal wing 21 may or may not extend outward beyond the superior side 26 of the body 23 in the closed orientation.

The body 23 follows the distal wing 21 and moves through the patient and is positioned within the L4/L5 interspinous space 101. The height of the body 23 may result in contact against an inferior side of the L4 spinous process 110 and against a superior side of the L5 spinous process 111. This contact may occur during the insertion into the patient, or may result after insertion with the surgeon rotating or otherwise positioning the body 23 within the interspinous space 101.

The proximal wing 27 does not pass through the interspinous space 101 and therefore may not include a reduced profile in the closed orientation. The proximal wing 27 is positioned on the near lateral side of the interspinous space 101. The proximal wing 27 may or may not extend outward above a superior side of the body 23 in the closed orientation.

The connector 60 is connected to the proximal wing 27 and extends outward in a posterior direction when the implant 10 is in the closed orientation. The connector 60 may be connected to the proximal wing 27 prior to or after insertion of the first member 20 into the patient.

The second member 40 is placed in the closed orientation and inserted in the L5/S1 interspinous space 103. The tapered shape of the distal wing 41 facilitates insertion into the patient and is sized to pass through the interspinous space 103 and be positioned on the far lateral side. The body 43 may fit within the profile of the distal wing 41 and follow into the space 103. The height of the body 43 may provide for contact with the inferior side of the L5 spinous process 114 and the superior side of the S1 spinous process 115 during initial insertion in the patient. Alternatively, the surgeon may rotate or otherwise position the body 43 after insertion to provide this contact. In cases where the S1 spinous process 115 is not prominent, the body 43 may contact the posterior portion of the S1 vertebral member 112. The proximal wing 47 does not move through the interspinous space 103 and therefore may not be positioned in the profile of the body 43 and/or the distal wing 41 in the closed orientation.

FIG. 2 illustrates the procedure with the superior and second members 20, 40 after being moved to the deployed orientations. Movement of the second member 40 includes the surgeon applying a rotational force to the proximal wing 47. This force rotates the proximal wing 47 and aligns the slot 49 along the posterior side and the superior side of the proximal wing 47. The proximal wing 47 also extends outward beyond a superior side of the body 43 with the inner face 52 facing towards the lateral side of the L5 spinous process 114. The amount of rotation between the closed and deployed orientations may vary. One embodiment includes rotation of about 90°. The first and second members 20, 40 may include the same or different amounts of rotation between the closed and deployed orientations.

Rotation of the proximal wing 47 also rotates the distal wing 41 because the distal wing 41 is connected to the proximal wing 47 by the extension 48 (FIG. 7). The distal wing 41 extends outward beyond the superior side 46 of the body 43 with the inner face 53 facing towards the lateral side of the L5 spinous process.

The wings 41, 47 control the extent of lateral movement of the second member 40. One or both of the wings 41, 47 may extend outward beyond the superior side 46 of the body 43 in the closed orientation. These wings 41, 47 now extend farther outward from the superior side 46 in the deployed orientation.

For the first member 20, movement to the deployed orientation may occur by the surgeon applying a rotational force to the connector 60 or directly to the proximal wing 27. Rotation of the proximal wing 27 further causes rotation of the connected extension 28 (FIG. 3) and the distal wing 21. This force does not rotate the body 23 because the extension 28 extends through and can rotate in the aperture 24 (FIG. 3).

Rotation further moves the connector 60 into the slot 49 in the proximal wing 47 of the second member 40. The length of the connector 60 may position the second end 62 within proximal wing 47, or on a far side opposite from the first member 20.

Once the connector 60 is positioned within the slot 49, a set screw 65 secures the connector 60 to the proximal wing 47. The set screw 65 may fit within the threaded enlarged section 50 of the slot 49. The set screw 65 may apply a force to maintain the connector 60 against the bottom wall 51 of the slot 49. Further, the set screw 31 may be tightened onto the second cavity 30 in the proximal wing 27. The set screw 31 contacts against the rounded head to further maintain the position of the connector 60.

Once the connector 60 is secured, the implant 10 may be further positioned by the surgeon as necessary. At this time, the implant 10 is securely connected together and is moved as a single unit As illustrated in FIGS. 2 and 11, the implant 10 may be inserted with a unilateral approach with distraction necessary on just the first lateral side of the spine. The implant 10 is implanted without requiring distraction of tissue on the second lateral side of the spine.

The method described above includes the implant 10 implanted into the patient with the first and second members 20, 40 being separately implanted and then connected together with the connector 60. Another procedure includes the members 20, 40 being connected together with the connector 60 prior to being implanted into the patient. The entire implant 10 is then inserted together into the patient with the various elements being placed within the appropriate interspinous spaces. In this procedure, the members 20, 40 may be placed in the deployed orientations prior to insertion into the patient.

The procedure described in FIGS. 2 and 11 include the connector 60 connected to the first member 20 and positioned within a slot 49 in the second member 40. The implant 10 may also include the connector 60 connected to and extending outward from the second member 40 and positioned within a receiver in the first member 20. Further, the member 20 may be positioned inferiorly from the member 40.

The procedure described above includes positioning the implant 10 at the L4-S1 levels of the spine. This facilitates positioning of the second member 40 in the L5/S1 interspinous space 103 because of the anatomical issues with the S1 spinous process 115. The implant 10 may also be positioned at different levels of the spine as necessary to treat a spinal defect. Applications may also include other levels of the lumbar region, and also levels of the cervical and thoracic regions.

The superior and second members 20, 40 may include a common construction each with distal wings, bodies, and proximal wings. The shapes and sizes of the elements of the members 20, 40 may vary because of the positioning at different spinal levels. In one embodiment, the distal wings and bodies of the members 20, 40 are substantially identical.

The implants 10 may be implanted within a living patient for the treatment of various spinal disorders. The implant 10 may also be implanted in a non-living situation, such as within a cadaver, model, and the like. The non-living situation may be for one or more of testing, training, and demonstration purposes.

The elements of the implant 10 are positioned in the patient to contact against the various vertebral members. This contact may include direct contact with the implant actually touching the vertebral members, and may also include indirect contact with the implant 10 actually touching the surrounding ligaments and tissue. In both instances, the implant 10 includes a similar effectiveness for treating the spinal disorder for which it was implanted.

The first and second members 20, 40 may be positioned at immediately adjacent spinal levels. For example, the first member 20 may be positioned in the L2/L3 interspinous space and the second member 40 may be positioned in the L3/L4 interspinous space. Additionally, the members 20, 40 may be spaced apart at more distant spinal levels (e.g., first member 20 at L1/L2 and second member 40 at L4/L5). The spacing may be controlled by the size and shape of the connector 60. In the more distant spacing contexts, the immediate vertebral members may still remain in the patient, or one or more may be removed from the patient.

The first member 20 may also be used as a stand alone device. The connector 60 that extends outward from the proximal wing 27 may be used to maintain the lateral position of the member 20 within the patient. The stand alone first member 20 may be used at various locations along the spine.

The term "distal" is generally defined as in the direction of the patient, or away from a user of a implant. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the implant in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A multi-level interspinous implant comprising:
   first and second members that each include a body positioned between a distal wing and a proximal wing, the bodies each including a superior side and an inferior side, the distal and proximal wings of the first member being connected together by a first extension that extends through the first member body and the wings of the second member being connected together by a second extension that extends through the second member body, the members being individually rotatable from a closed orientation with the distal wing aligned with the body and a deployed orientation with both the distal and proximal wings extending outward beyond the superior side of the body to maintain a lateral position of the members, the proximal wing of the first member defines an axis, the proximal wing of the second member is disposed along the axis;
   a connector with an elongated length and first and second ends, the first end connected to the proximal wing of the first member and the second end positioned away from the proximal wing of the first member, the proximal wing of the first member is configured to rotate along the axis towards the proximal wing of the second member such that the connector engages the proximal wing of the second member in substantially perpendicular alignment;
   a slot that extends into the proximal wing of the second member and includes a width configured to receive the connector, the slot positioned in a posterior side and at least one of the superior and inferior sides of the proximal wing of the second member when the second member is in the deployed orientation, such that the second end of the connector is configured to be adjustable between being disposed within the proximal wing of the second member and extending past an inferior side of the proximal wing of the second member allowing for proper adjustment of the first and second members;
   the connector extending outward in a posterior direction from the proximal wing of the first member and away from the second member when the first member is in the closed orientation, and positioned in the slot when the first member is in the deployed orientation;
   wherein the proximal wing of the first member includes a first cavity on a first side sized to receive the first end of the connector and a second cavity on a second side that is in communication with the first cavity.

2. The implant of claim 1, wherein a trailing end of the distal wing and the body of the first member each include an elongated shape with a major axis and a minor axis, the major axes being parallel when the first member is in the closed orientation and are nonparallel when the first member is in the deployed orientation.

3. The implant of claim 1, wherein the distal wings and the bodies of the first and second members are substantially identical.

4. The implant of claim 1, wherein the first body includes a first aperture through which the first extension extends and the second body includes a second aperture through which the second extension extends, the apertures being sized for the extensions to rotate in the bodies when the members move from the closed orientation to the deployed orientation without rotating the bodies.

5. The implant of claim 1, wherein the connector extends outward from an inferior side of the first member when the first member is in the deployed orientation.

6. The implant of claim 1, wherein the distal wings of the members extend outward beyond the superior sides of the bodies when the members are in the closed orientations.

7. A multi-level interspinous implant comprising:
a superior member with a first body positioned between a first distal wing and a first proximal wing, the first body including a superior side to contact against an inferior side of a first spinous process and an inferior side to contact against a superior side of a second spinous process, the proximal wing of the superior member defines an axis, the first distal and proximal wings being connected together by an extension that extends through the first body and are movable from a closed orientation and a deployed orientation with the first distal wing extending above the superior side of the first body in the deployed orientation, the first proximal wing also extending outward beyond the superior side of the body in the deployed orientation;
an elongated connector having a first end and a second end that extends outward from an inferior side of the first proximal wing;
an inferior member with a second body positioned between a second distal wing and a second proximal wing, the proximal wing of the inferior member being disposed along the axis, the second body including a superior side to contact against an inferior side of the second first spinous process and an inferior side to contact against a superior side of a second spinous process, the second distal and proximal wings being connected together by an extension that extends through the second body and are movable from a closed orientation and a deployed orientation with the second distal wing extending above the superior side of the second body in the deployed orientation, the second proximal wing also extending outward beyond the superior side of the second body in the deployed orientation, the second proximal wing including a slot that extends into posterior and superior sides, the slot including a width to receive the connector;
the first proximal wing being movable from the closed orientation with the connector extending outward in a posterior direction to the open position with the connector positioned in the slot of the second proximal wing and positioned to extend along a lateral side of the second spinous process, the proximal wing of the superior member is configured to rotate along the axis towards the proximal wing of the inferior member such that the elongated connector engages the slot of the proximal wing of the inferior member in substantially perpendicular alignment, such that the second end of the connector is adjustable between being disposed within the proximal wing of the second member and extending past an inferior side of the proximal wing of the second member allowing for proper adjustment of the first and second members;
wherein the first proximal wing includes a first cavity sized to receive the connector, and a second cavity that is in communication with the first cavity.

8. The implant of claim 7, wherein the connector includes a round head at a first end positioned in the first cavity in the first proximal wing, the round head and the first cavity sized for the connector to be pivotally connected to the first proximal wing.

9. The implant of claim 8, wherein the further comprising a second cavity extends into the first proximal wing from a different direction than the first cavity the second cavity and the cavity being in communication in the first proximal wing.

10. The implant of claim 7, wherein the extension of the first proximal wing extends through the first body along a line that is offset from a longitudinal axis of the first body.

11. The implant of claim 7, wherein the first distal wing and the first body each include an elongated shape with a major axis and a minor axis, the major axes being parallel when the superior member is in the closed orientation and are non-parallel when the superior member is in the deployed orientation.

12. A method of treating a spinal disorder of a patient using the device of claim 1 comprising: unilaterally inserting the first member while in a closed orientation into the patient and positioning the first distal wing on a first lateral side of a first interspinous space, positioning the first body in the first interspinous space, and positioning the first proximal body on a second lateral side of the first interspinous space, each of the first distal wing, first body, and first proximal body being connected together and aligned along a first longitudinal axis; unilaterally inserting the second member while in a closed orientation into the patient and positioning the second distal wing on the first lateral side of a second interspinous space, positioning the second body in a second interspinous space, and positioning the second proximal body on a second lateral side of the second interspinous space, each of the second distal wing, second body, and second proximal body being connected together and aligned along a second longitudinal axis; positioning the elongated connector that extends outward from the first proximal body away from the second member; moving the second member from the closed orientation to a deployed orientation by rotating the second distal wing and the second proximal wing relative to the second body and positioning sections of the second distal wing and the second proximal wing along opposing sides of the second spinous process; moving the first member from the closed orientation to the deployed orientation by rotating the first distal wing and the first proximal wing relative to the first body and positioning sections of the first distal wing and the first proximal wing along opposing sides of a first spinous process; and rotating the connector towards the second member and inserting the connector into the slot formed in superior and posterior sides of the second proximal wing and connecting the first member and the second member.

13. The method of claim 12, further comprising positioning a superior surface of the second body outward farther in a superior direction than the second distal wing when the second member is in the closed orientation.

14. The method of claim 12, wherein positioning the connector outward from the first proximal body away from the second member includes positioning the connector in a posterior direction when the first member is in the closed orientation.

15. The method of claim 12, wherein the connector is connected to the first proximal wing moving the first member from the closed orientation to the deployed orientation and inserting the connector into the slot occur simultaneously.

16. The method of claim 12, further comprising positioning the superior side of the second proximal wing away from the first member when the second member is in the closed orientation.

17. The method of claim 12, further comprising attaching a set screw to the second proximal wing and securing the connector in the slot.

18. The method of claim 12, further comprising pivotally moving the connector about a rounded head positioned in the first proximal wing prior to inserting the connector into the slot in the second proximal member.

19. The method of claim 12, wherein positioning the first body in the first interspinous space includes positioning the first body in a L4/L5 interspinous space and positioning the second body in the second interspinous space includes positioning the first body in a L5/S1 interspinous space.

\* \* \* \* \*